United States Patent
Fujikawa et al.

(10) Patent No.: US 10,155,824 B2
(45) Date of Patent: Dec. 18, 2018

(54) CARBOXYMETHYL-GROUP-CONTAINING MODIFIED HYALURONIC ACID AND/OR SALT THEREOF AND/OR PRODUCTION METHOD FOR CARBOXYMETHYL-GROUP-CONTAINING MODIFIED HYALURONIC ACID AND/OR SALT THEREOF

(71) Applicant: KEWPIE CORPORATION, Tokyo (JP)

(72) Inventors: Shunichi Fujikawa, Chofu (JO); Yukina Abe, Chofu (JP); Kazunori Asaoka, Chofu (JP); Takushi Yoshida, Chofu (JP)

(73) Assignee: KEWPIE CORPORATION, Tokyo (JP)

( * ) Notice: Subject to any disclaimer, the term of this patent is extended or adjusted under 35 U.S.C. 154(b) by 0 days.

(21) Appl. No.: 15/027,841

(22) PCT Filed: Oct. 7, 2014

(86) PCT No.: PCT/JP2014/076846
§ 371 (c)(1),
(2) Date: Apr. 7, 2016

(87) PCT Pub. No.: WO2015/053280
PCT Pub. Date: Apr. 16, 2015

(65) Prior Publication Data
US 2016/0244534 A1    Aug. 25, 2016

(30) Foreign Application Priority Data

Oct. 8, 2013  (JP) .................................. 2013-211480

(51) Int. Cl.
| C08B 37/08 | (2006.01) |
| A61K 47/36 | (2006.01) |
| C08L 5/08 | (2006.01) |
| A61Q 5/02 | (2006.01) |
| A61Q 5/12 | (2006.01) |
| A61K 8/73 | (2006.01) |
| A61Q 17/04 | (2006.01) |
| A61Q 19/00 | (2006.01) |
| A61Q 19/10 | (2006.01) |
| A61K 9/14 | (2006.01) |
| A61K 9/48 | (2006.01) |
| A23L 33/10 | (2016.01) |

(52) U.S. Cl.
CPC .......... *C08B 37/0072* (2013.01); *A23L 33/10* (2016.08); *A61K 8/735* (2013.01); *A61K 9/14* (2013.01); *A61K 9/4866* (2013.01); *A61K 47/36* (2013.01); *A61Q 5/02* (2013.01); *A61Q 5/12* (2013.01); *A61Q 17/04* (2013.01); *A61Q 19/00* (2013.01); *A61Q 19/007* (2013.01); *A61Q 19/10* (2013.01); *C08L 5/08* (2013.01); *A23V 2002/00* (2013.01); *A61Q 19/001* (2013.01)

(58) Field of Classification Search
None
See application file for complete search history.

(56) References Cited

U.S. PATENT DOCUMENTS

| 7,981,871 B2 * | 7/2011 | Prestwich ...................... 424/488 |
| 2009/0215719 A1 | 8/2009 | Yoshida |
| 2012/0128741 A1 | 5/2012 | Gravett et al. |
| 2012/0142907 A1 | 6/2012 | Prestwich et al. |

FOREIGN PATENT DOCUMENTS

| CN | 101225125 A | 7/2008 |
| CN | 102174122 A | 9/2011 |
| CN | 102573941 A | 7/2012 |
| CN | 102898545 A | 1/2013 |
| DE | 10 2005 004 643 A1 | 8/2006 |
| DE | 10 2009 024 616 A1 | 12/2010 |
| JP | 63-57602 A | 3/1988 |
| JP | 2007-520589 A | 7/2007 |
| JP | 2013-501091 A | 1/2013 |

OTHER PUBLICATIONS

Khalil, M. I., Hashem, A., & Hebeish, A. (1990). Carboxynnethylation of maize starch. Starch-Stärke, 42(2), 60-63. (Year: 1990).*

Moller et al., "Synthesis and antiherpetic activity of carboxymethylated and sulfated hyaluronan derivatives", Carbohydrate Polymers, vol. 90, 2012, pp. 608-615; cited in the ISR (in English).

Yang et al., "The hydroxyl radical scavenging activity of chitosan, hyaluronan, starch and their O-carboxymethylated derivatives", Carbohydrate Polymers, vol. 82, 2010, pp. 1042-1045; cited in the ISR (in English).

"The Japanese Pharmacopoeia", 14th edition, Hirokawa-Shoten, Ltd., 2006 (w/ partial English translation; 12 pages).

Laurent et al., "Fractionation of Hyaluronic Acid the Polydispersity of Hyaluronic Acid From the Bovine Vitreous Body", Biochimica Et Biophysica Acta, vol. 42, 1960, pp. 476-485 (w/ partial English translation).

(Continued)

*Primary Examiner* — Shaojia A Jiang
*Assistant Examiner* — Dale R Miller
(74) *Attorney, Agent, or Firm* — Westerman, Hattori, Daniels & Adrian, LLP

(57) ABSTRACT

A method of producing a carboxymethyl-group-containing modified hyaluronic acid and/or a salt thereof includes a step of subjecting, in a water-containing solvent having a temperature of 30° C. or less, a dissolved raw material hyaluronic acid and/or a salt thereof to a reaction with a haloacetic acid and/or a salt thereof, the water-containing solvent including water or a liquid mixture of a water-soluble organic solvent and water, a ratio of the water-soluble organic solvent in the liquid mixture being 60 v/v % or less.

12 Claims, 3 Drawing Sheets

(56) References Cited

OTHER PUBLICATIONS

Yomota, "Evalution of Molecular Weights of Hyaluronate Preparations by multi-Angle Light Scattering", Bull. Natl. Inst. Health Sci., vol. 121, 2003, pp. 030-033 (w/ partial English translation).
International Search Report and Written Opinion dated Jan. 6, 2015 issued in corresponding application No. PCT/JP2014/076846; w/ English partial translation and partial machine translation (12 pages).
Chinese Office Action dated Jun. 2, 2017 in counterpart Chinese application No. 201480055355.9; with English machine translation (20 pages) (D1-D5, D8 and D10 cited in the Chinese Office Action are not listed in this IDS since they were already listed in the IDS filed Apr. 7, 2016).
Kiao Zheng Shu et al., "Disulfide Cross-Linked Hyaluronan Hydrogels", Biomacromolecules, vol. 3, No. 6, 2002, p. 1304-p. 1311 (in English).
Guanghui Yang et al., "Thiolated Carboxymethyl-Hyaluronic-Acid-Based Biomaterials Enhance Wound Healing in Rats, Dogs and Horses", International Scholarly Research Network ISRN Veterinary Science, 2011, p. 1-p. 7 (in English).

* cited by examiner

CARBOXYMETHYL-GROUP-CONTAINING MODIFIED HYALURONIC ACID AND/OR SALT THEREOF AND/OR PRODUCTION METHOD FOR CARBOXYMETHYL-GROUP-CONTAINING MODIFIED HYALURONIC ACID AND/OR SALT THEREOF

TECHNICAL FIELD

The present invention relates to a carboxymethyl-group-containing modified hyaluronic acid and/or a salt thereof and/or a production method therefor, and a cosmetic, a food composition, and a pharmaceutical composition containing the same.

BACKGROUND ART

Many water-soluble polysaccharides, such as hyaluronic acid, contain hydroxyl groups or carboxyl groups and have a high viscosity due to a hydrogen bond formed between the groups (JP S63-57602 A). The high viscosity of the water-soluble polysaccharide may cause an unfavorable feeling of touch in pharmaceuticals for external use and cosmetics and may cause an unfavorable texture in pharmaceuticals for oral administration and foods. Therefore, a water-soluble polysaccharide having a water retention ability, less stickiness, and an excellent texture has been required.

SUMMARY OF INVENTION

Technical Problem

The present invention provides a method of producing a carboxymethyl-group-containing modified hyaluronic acid and/or a salt thereof by which a carboxymethyl-group-containing modified hyaluronic acid having a high degree of whiteness and a high carboxymethylation ratio can be easily obtained.

The present invention also provides a carboxymethyl-group-containing modified hyaluronic acid and/or a salt thereof having a high degree of whiteness and a high carboxymethylation ratio, and a cosmetic, a food composition, and a pharmaceutical composition each containing the same.

Solution to Problem

The inventors of the present application have found that a modified hyaluronic acid having a high degree of whiteness and a predetermined carboxymethylation ratio can be obtained by subjecting a hyaluronic acid to a reaction with a haloacetic acid and/or a salt thereof under specific conditions.

The inventors of the present application have also found that a carboxymethyl-group-containing modified hyaluronic acid and/or a salt thereof obtained by such method has a high degree of whiteness, a high water retention ability, and a low viscosity.

1. A method of producing a carboxymethyl-group-containing modified hyaluronic acid and/or a salt thereof according to one aspect of the present invention includes a step of subjecting, in a water-containing solvent having a temperature of 30° C. or less, a dissolved raw material hyaluronic acid and/or a salt thereof to a reaction with a haloacetic acid and/or a salt thereof, the water-containing solvent including water or a liquid mixture of a water-soluble organic solvent and water, a ratio of the water-soluble organic solvent in the liquid mixture being 60 v/v % or less.

2. In the method of producing a carboxymethyl-group-containing modified hyaluronic acid and/or a salt thereof according to Item 1, the haloacetic acid may be chloroacetic acid and/or bromoacetic acid.

3. In the method of producing a carboxymethyl-group-containing modified hyaluronic acid and/or a salt thereof according to Item 1 or 2, a concentration of the hyaluronic acid in the water-containing solvent may be 0.05 g/mL or more and 0.5 g/mL or less.

4. In the method of producing a carboxymethyl-group-containing modified hyaluronic acid and/or a salt thereof according to anyone of Items 1 to 3, the dissolved raw material hyaluronic acid and/or the salt thereof may have a molecular weight of 4,000 or more and 4,000,000 or less.

5. The method of producing a carboxymethyl-group-containing modified hyaluronic acid and/or a salt thereof according to any one of Items 1 to 4, the carboxymethyl-group-containing modified hyaluronic acid and/or the salt thereof to be obtained may have a b value indicating a hue of a color of 5 or less.

6. In the method of producing a carboxymethyl-group-containing modified hyaluronic acid and/or a salt thereof according to anyone of Items 1 to 5, the reaction step may provide a carboxymethyl-group-containing modified hyaluronic acid having a molecular weight of 800,000 or more.

7. In the method of producing a carboxymethyl-group-containing modified hyaluronic acid and/or a salt thereof according to Item 6, the reaction step may provide a carboxymethyl-group-containing modified hyaluronic acid having a carboxymethylation ratio to disaccharide units constituting the hyaluronic acid of 5% or more and 200% or less.

8. A carboxymethyl-group-containing modified hyaluronic acid and/or a salt thereof according to one aspect of the present invention has a molecular weight of 800,000 or more and a carboxymethylation ratio to disaccharide units constituting the hyaluronic acid of 5% or more and 200% or less.

9. The carboxymethyl-group-containing modified hyaluronic acid and/or the salt thereof according to Item 8 may have a kinetic viscosity of 30 mm$^2$/s or more and 200 mm$^2$/s or less.

10. In the carboxymethyl-group-containing modified hyaluronic acid and/or the salt thereof according to Item 8 or 9, a hydrogen atom of at least a part of hydroxyl groups constituting the hyaluronic acid may be substituted with a group represented by —$CH_2$—$CO_2H$ and/or —$CH_2$—$CO_2^-$.

11. The carboxymethyl-group-containing modified hyaluronic acid and/or the salt thereof according to any one of Items 8 to 10 may have a b value indicating a hue of a color of 5 or less.

12. In the method of producing a carboxymethyl-group-containing modified hyaluronic acid and/or a salt thereof according to anyone of Items 1 to 5, the reaction step may provide a carboxymethyl-group-containing modified hyaluronic acid having a molecular weight of 4,000 or more and less than 800,000.

13. In the method of producing a carboxymethyl-group-containing modified hyaluronic acid and/or a salt thereof according to Item 12, the reaction step may provide a carboxymethyl-group-containing modified hyaluronic acid having a carboxymethylation ratio to disaccharide units constituting the hyaluronic acid of 60% or more and 200% or less.

14. A carboxymethyl-group-containing modified hyaluronic acid and/or a salt thereof according to one aspect of the present invention may provide a carboxymethyl-group-containing modified hyaluronic acid having a molecular weight of 4,000 or more and less than 800,000 and a carboxymethylation ratio to disaccharide units constituting the hyaluronic acid of 60% or more and 200% or less.

15. The carboxymethyl-group-containing modified hyaluronic acid and/or the salt thereof according to Item 14 may have a kinetic viscosity of 1 $mm^2/s$ or more and 200 $mm^2/s$ or less.

16. In the carboxymethyl-group-containing modified hyaluronic acid and/or the salt thereof according to Item 14 or 15, a hydrogen atom of at least a part of hydroxyl groups constituting the hyaluronic acid may be substituted with a group represented by $—CH_2—CO_2H$ and/or $—CH_2—CO_2^-$.

17. The carboxymethyl-group-containing modified hyaluronic acid and/or the salt thereof according to any one of Items 14 to 16 may have a b value indicating a hue of a color of 5 or less.

18. A cosmetic according to one aspect of the present invention includes the carboxymethyl-group-containing modified hyaluronic acid and/or the salt thereof of any one of Items 8 to 11 and 14 to 17.

19. A food composition according to one aspect of the present invention includes the carboxymethyl-group-containing modified hyaluronic acid and/or the salt thereof of any one of Items 8 to 11 and 14 to 17.

20. A pharmaceutical composition according to one aspect of the present invention includes the carboxymethyl-group-containing modified hyaluronic acid and/or the salt thereof of any one of Items 8 to 11 and 14 to 17.

Advantageous Effects of Invention

According to the methods of producing a carboxymethyl-group-containing modified hyaluronic acid and/or a salt thereof according to Items 1 to 7, 12, and 13, the method includes a step of subjecting, in a water-containing solvent having a temperature of 30° C. or less, a dissolved raw material hyaluronic acid and/or a salt thereof to a reaction with a haloacetic acid and/or a salt thereof, in which the water-containing solvent is water or a liquid mixture of the water-soluble organic solvent and water and a ratio of the water-soluble organic solvent in the liquid mixture is 60 v/v % or less, with the result that a modified hyaluronic acid having a high degree of whiteness and a predetermined carboxymethylation ratio can be easily obtained.

The carboxymethyl-group-containing modified hyaluronic acids and/or the salt thereof according to Items 8 to 11 has a molecular weight of 800,000 or more and a carboxymethylation ratio to disaccharide units constituting the hyaluronic acid of 5% or more and 200% or less, and the carboxymethyl-group-containing modified hyaluronic acids and/or the salt thereof according to Items 14 to 17 has a molecular weight of 4,000 or more and less than 800,000 and a carboxymethylation ratio to disaccharide units constituting the hyaluronic acid of 60% or more and 200% or less. Therefore, the carboxymethyl-group-containing modified hyaluronic acids and/or the salts thereof each have a water retention ability and a low viscosity compared to a hyaluronic acid having a similar molecular weight. Accordingly, the carboxymethyl-group-containing modified hyaluronic acids and/or the salts thereof each have a high degree of whiteness, less stickiness, a good feeling of touch (light feeling), and a good texture, and hence can be used as ingredients of, for example, pharmaceuticals, cosmetics, and foods.

DESCRIPTION OF EMBODIMENTS

Figure 1:
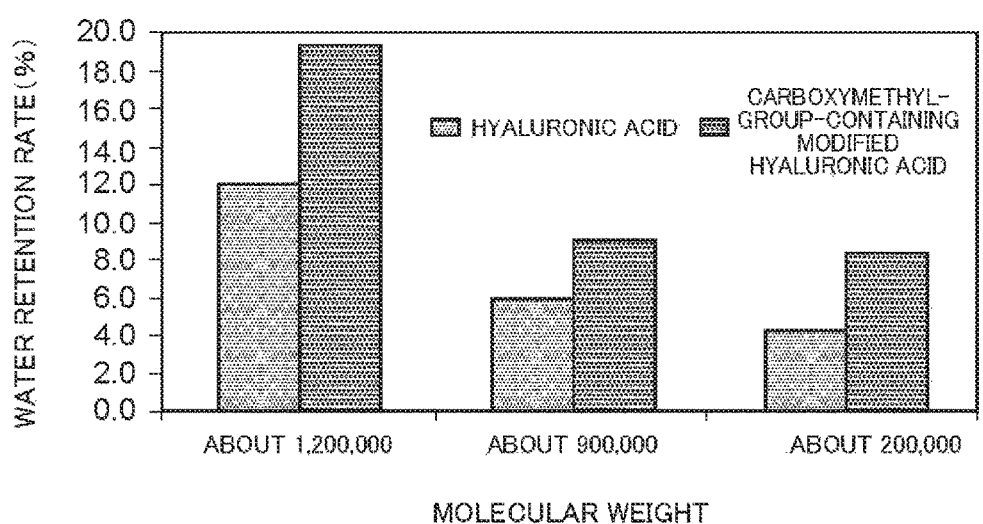
FIG. 1 is a graph for showing results of measurement of a water retention rate of a carboxymethyl-group-containing modified hyaluronic acid and/or a salt thereof according to one example of the present invention.

The present invention is hereinafter described in detail with reference to the drawings. In the present invention, "part(s)" means "part(s) by mass" and "%" means "mass %" unless otherwise specified.

[Method of Producing Carboxymethyl-Group-Containing Modified Hyaluronic Acid and/or Salt Thereof]

A method of producing a carboxymethyl-group-containing modified hyaluronic acid and/or a salt thereof (sometimes referred to simply as "modified hyaluronic acid" herein) according to one embodiment of the present invention includes a step of subjecting, in a water-containing solvent having a temperature of 30° C. or less, a dissolved raw material hyaluronic acid and/or a salt thereof to a reaction with a haloacetic acid and/or a salt thereof. In this step, the water-containing solvent is water or a liquid mixture of the water-soluble organic solvent and water, and the ratio of the water-soluble organic solvent in the liquid mixture is 60 v/v % or less.

In the reaction step, the hyaluronic acid and/or the salt thereof may be subjected to a reaction with the haloacetic acid and/or the salt thereof in a state in which at least part of the hyaluronic acid and/or the salt thereof (preferably, the whole or most part of the hyaluronic acid and/or the salt thereof) and the haloacetic acid and/or the salt thereof are dissolved in the reaction liquid (water-containing solvent). In this case, the reaction liquid may be transparent when visually observed because the hyaluronic acid and/or the salt thereof and the haloacetic acid and/or the salt thereof are dissolved.

<Raw Material Hyaluronic Acid and/or Salt Thereof>

In the present invention, the term "hyaluronic acid" refers to a polysaccharide having at least one repeating structural unit consisting of a disaccharide of a glucuronic acid and an N-acetylglucosamine. In addition, the "salt of hyaluronic acid" is not particularly limited, and is preferably an acceptable salt in food or pharmacy. Examples thereof include a sodium salt, a potassium salt, a calcium salt, a zinc salt, a magnesium salt, and an ammonium salt.

Hyaluronic acid is basically a disaccharide or a polysaccharide, which includes at least one disaccharide unit in which a C-1 position of a β-D-glucuronic acid and a C-3 position of a β-D-N-acetyl-glucosamine are bonded to each other, is basically formed of a β-D-glucuronic acid and a β-D-N-acetyl-glucosamine, and has a plurality of the disaccharide units bonded to each other. The disaccharide or the polysaccharide may be an unsaturated sugar, and an example of the unsaturated sugar is a sugar having a non-reducing end, typically, a sugar having an unsaturated bond between a C-4 position and a C-5 position of a glucuronic acid.

A raw material hyaluronic acid and/or a salt thereof to be used as a raw material in the production method according to the embodiment may be: an extract from natural products such as animals (for example, a biological tissue such as a cockscomb, an umbilical cord, skin, or synovial fluid); a culture product obtained by culturing microorganisms, animal cells, or plant cells (for example, a fermentation method using a bacterium belonging to the genus *Streptococcus* or the like); or a chemically or enzymatically synthesized product.

As the raw material hyaluronic acid and/or the salt thereof, both of the crude extract and the purified product may be used, and the purified product, specifically, a raw material hyaluronic acid and/or a salt thereof having a purity of 90% (by mass) or more is preferably used because carboxymethylation can progress smoothly.

<Average Molecular Weight of Raw Material Hyaluronic Acid and/or Salt Thereof>

In the production method according to the embodiment, the raw material hyaluronic acid and/or the salt thereof to be dissolved in the reaction step typically has an average molecular weight of preferably 4,000 or more and 4,000,000 or less, more preferably 3,000,000 or less because carboxymethylation can be performed smoothly. The average molecular weight of the raw material hyaluronic acid and/or the salt thereof can be measured by the following method.

<Method of Measuring Molecular Weight>

Specifically, about 0.05 g of a (purified) hyaluronic acid (substance) is weighed accurately and dissolved in a 0.2 mol/L sodium chloride solution to prepare exactly 100 mL of the resultant solution. The solution is weighed exactly in amounts of 8 mL, 12 mL, and 16 mL, and a 0.2 mol/L sodium chloride solution is added to the respective solutions to prepare exactly 20 mL of the resultant solutions as sample solutions. The specific viscosity of each of the sample solutions and the 0.2 mol/L sodium chloride solution is measured at 30.0±0.1° C. by a viscosity measurement method (first method, capillary viscosity measurement method) of general test methods of the Japanese Pharmacopoeia (16th edition) (Expression (A)), and the reduced viscosity at each concentration is calculated (Expression (B)). The reduced viscosity and the concentration of the substance calculated on the dried basis (g/100 mL) are plotted on the vertical axis and the horizontal axis, respectively, of a graph, and the limiting viscosity is calculated from the intersection point of a straight line that connects each point and the vertical axis. The determined limiting viscosity is substituted into the Laurent Expression (Expression (C)) to calculate its average molecular weight (Torvard C Laurent, Marion Ryan, and Adolph Pietruszkiewicz, "Fractionation of hyaluronic Acid," Biochemical et Biophysical Acta., 42, 476-485 (1960); Chikako Yomota, "Evaluation of Molecular Weights of Sodium Hyaluronate Preparations by SEC-MALLS," Bull. Natl. Inst. Health Sci., 121, 030-033 (2003)).

Specific viscosity={required number of seconds for flowing down of sample solution}/{required number of seconds for flowing down of 0.2 mol/L sodium chloride solution)}−1   (Expression A)

Reduced viscosity (dL/g)=specific viscosity/(concentration of substance calculated on dried basis (g/100 mL))   (Expression B)

Limiting viscosity (dL/g)=$3.6 \times 10^{-4} M^{0.78}$   (Expression C)

M: Average molecular weight

<Content of Raw Material Hyaluronic Acid and/or Salt Thereof>

In the raw material hyaluronic acid and/or the salt thereof, the content of the raw material hyaluronic acid and/or the salt thereof is an indicator of the purity of the raw material hyaluronic acid and/or the salt thereof, and it can be said that as the content of the raw material hyaluronic acid and/or the salt thereof becomes higher, the purity of the raw material hyaluronic acid and/or the salt thereof becomes higher.

In the present invention, the content of the hyaluronic acid in the raw material hyaluronic acid and/or the salt thereof is a value that is calculated from a quantitative value of glucuronic acid measured by a carbazole-sulfuric acid method (for example, the Japanese Pharmacopoeia).

The carbazole-sulfuric acid method is a method involving adding an aqueous solution of a hyaluronic acid to a sodium borate-sulfuric acid solution, mixing the solution to degrade the hyaluronic acid while heating, cooling the solution, adding a carbazole-ethanol solution, mixing the solution, heating and then cooling the solution, and measuring an absorbance (530 nm) of the resultant sample solution. The same process is performed with D-glucuronolactone, a calibration curve is prepared to calculate a value in terms of D-glucuronolactone, and then a quantitative value of glucuronic acid is calculated by multiplying the value in terms of D-glucuronolactone by 1.102. The content of the hyaluronic acid is calculated by multiplying the obtained quantitative value of glucuronic acid by (the molecular weight of the hyaluronic acid/the molecular weight of glucuronic acid).

<Carboxymethylation>

In the present invention, the term "modified hyaluronic acid and/or a salt thereof" refers to a hyaluronic acid and/or a salt thereof having an organic group introduced into at least part thereof and having a structure different from that of a hyaluronic acid and/or a salt thereof. In the present invention, the term "organic group" refers to a group having a carbon atom.

In addition, in the present invention, the term "carboxymethyl group" refers to a group represented by "—$CH_2$—$CO_2H$" or "—$CH_2$—$CO_2^-$."

Therefore, in the present invention, the term "carboxymethyl-group-containing modified hyaluronic acid and/or a salt thereof" refers to a hyaluronic acid and/or a salt thereof having a carboxymethyl group introduced into at least part thereof.

More specifically, in the modified hyaluronic acid according to the embodiment, for example, a hydrogen atom of at least part of hydroxyl groups of hydroxyl groups (in the following formula (1), a C-4 position and a C-6 position of a N-acetylglucosamine constituting the hyaluronic acid and a C-2 position and a C-3 position of a glucuronic acid constituting the hyaluronic acid) constituting the hyaluronic acid (see the following formula (1)) may be substituted with a group represented by —$CH_2$—$CO_2H$ and/or —$CH_2$—$CO_2^-$. That is, in the modified hyaluronic acid according to the embodiment, hydrogen atoms of hydroxyl groups located at one or two or more positions of the hydroxyl groups located at the above-mentioned positions may be substituted with a group represented by —$CH_2$—$CO_2H$ and/or —$CH_2$—$CO_2^-$.

In the present invention, the term "disaccharide unit constituting the hyaluronic acid" refers to one unit including two saccharides (a glucuronic acid and an N-acetylglucosamine) adjacently bonded to each other, and the term "carboxymethylation ratio to disaccharide units constituting the hyaluronic acid" refers to the number of carboxymethyl groups contained in the one unit with respect to the one unit. More specifically, the term refers to a ratio (%) of the number of carboxymethyl groups contained in the one unit with respect to the one unit when the one unit is defined as 100%.

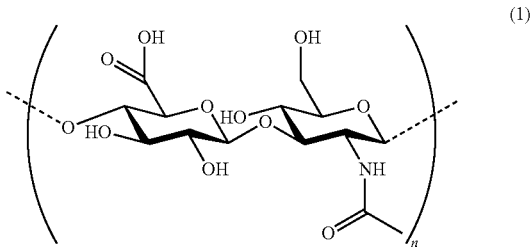

(1)

(In the formula, n represents a number of 1 or more and 7,500 or less.)

The modified hyaluronic acid according to the embodiment may be, for example, a compound represented by the following formula (2).

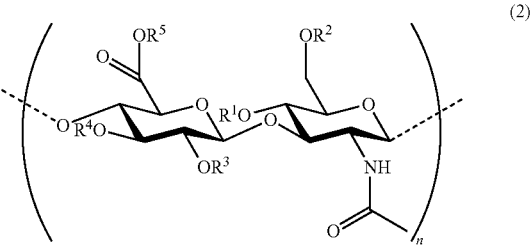

(2)

(In the formula, R1 to R5 each independently represent a hydrogen atom, a group represented by —CH2-CO2H, or a group represented by —CH2-CO2- (provided that a case where all of R1 to R5 represent a hydroxyl group hydrogen atom is excluded), and n represents a number of 1 or more and 7,500 or less.)

<pH>

In the production method according to the embodiment, the reaction is preferably carried out under a basic condition because nucleophilicity of the hydroxyl group can be enhanced, and it is more preferred that the reaction liquid (water-containing solvent) have a pH of 9 or more (9 or more and 14 or less, preferably 10 or more and 14 or less, more preferably 11 or more and 14 or less).

To adjust the reaction liquid to be basic, a basic electrolyte may be used in the reaction liquid. Examples of the basic electrolyte include: an alkali metal hydroxide, such as sodium hydroxide or potassium hydroxide; and an alkaline earth metal hydroxide, such as calcium hydroxide, magnesium hydroxide, or barium hydroxide. The concentration of the basic electrolyte in the reaction liquid is, for example, 0.2 mol/L or more and 10 mol/L or less, preferably 0.5 mol/L or more and 8 mol/L or less because both of the modified hyaluronic acid of the first example and the modified hyaluronic acid of the second example to be described below can be efficiently obtained.

In addition, the concentration of the hyaluronic acid in the water-containing solvent is preferably 0.05 g/mL or more and 0.5 g/mL or less because both of the modified hyaluronic acid of the first example and the modified hyaluronic acid of the second example to be described below can be efficiently obtained.

<Haloacetic Acid and/or Salt Thereof>

In the method of producing a modified hyaluronic acid according to the embodiment (hereinafter sometimes abbreviated simply as "production method according to the embodiment"), a haloacetic acid and/or a salt thereof is used for introducing a carboxymethyl group into the raw material hyaluronic acid and/or the salt thereof.

The haloacetic acid may be, for example, a monohaloacetic acid and/or a salt thereof, and more specifically, may be preferably chloroacetic acid and/or a salt thereof, or bromoacetic acid or a salt thereof. For example, the salt of the haloacetic acid is preferably an alkali metal salt of chloroacetic acid and/or an alkali metal salt of bromoacetic acid, more preferably sodium chloroacetate and/or sodium bromoacetate.

<Usage Amount of Haloacetic Acid and/or Salt Thereof>

The usage amount of the haloacetic acid and/or the salt thereof is typically 10% or more and 500% or less (by mass), preferably 50% or more and 200% or less (by mass) with respect to the usage amount of the raw material hyaluronic acid and/or the salt thereof.

<Water-Containing Solvent>

When the water-containing solvent used in the production method according to the embodiment is water or a liquid mixture of a water-soluble organic solvent and water, the raw material hyaluronic acid and/or the salt thereof is excellent insolubility.

When the water-containing solvent is a liquid mixture of the water-soluble organic solvent and water, that is, when the water-containing solvent contains both water and the water-soluble organic solvent, the ratio of the water-soluble organic solvent in the water-containing solvent is typically 60 v/v % or less (more than 0 v/v % and 60 v/v % or less), preferably 40 v/v % or less (more than 0 v/v % and 40 v/v % or less) because the solubility of the hyaluronic acid can be enhanced.

Examples of the water-soluble organic solvent may include: alcohol-based solvents, such as methanol, ethanol, 1-propanol, and 2-propanol; ketone-based solvents, such as acetone and methyl ethyl ketone; tetrahydrofuran; and acetonitrile. Only one kind or a combination thereof may be used. Of those, a lower alcohol having 1, 2, or 3 carbon atoms, such as isopropanol or ethanol, is preferred.

<Reaction Temperature>

In the reaction, typically, the temperature of the reaction liquid is preferably 30° C. or less (preferably more than 0° C. and 30° C. or less), more preferably 10° C. or less (preferably more than 0° C. and 30° C. or less) because carboxylation can proceed smoothly and a reduction in molecular weight can be suppressed. In particular, when the temperature of the reaction liquid is adjusted to 10° C. or less, a modified hyaluronic acid having a high molecular weight (800,000 or more) can be easily obtained.

For example, when chloroacetic acid and/or a salt thereof is used as the haloacetic acid and/or the salt thereof, in general, the temperature of the reaction liquid in the reaction may be 30° C. or less (preferably more than 0° C. and 30° C. or less) and is more preferably 1° C. or more and 30° C. or less because carboxymethylation can proceed smoothly and browning of the modified hyaluronic acid obtained can be suppressed.

In addition, for example, when bromoacetic acid and/or a salt thereof is used as the haloacetic acid and/or the salt thereof, the temperature of the reaction liquid in the reaction may be typically 10° C. or less (preferably more than 0° C. and 10° C. or less) and is preferably 1° C. or more and 10° C. or less because carboxymethylation can proceed smoothly and browning and a reduction in molecular weight of the modified hyaluronic acid obtained can be suppressed.

More specifically, in order to produce a modified hyaluronic acid having a high molecular weight (for example, having a molecular weight of 800,000 or more) and a high carboxymethylation ratio to disaccharide units constituting the hyaluronic acid (hereinafter sometimes referred to simply as "carboxymethylation ratio") (for example, 50% or more, preferably 50% or more and 200% or less), which is the first example to be described below, the reaction is preferably carried out using bromoacetic acid and/or a salt thereof as the haloacetic acid and/or the salt thereof at a reaction liquid temperature of 10° C. or less (for example, more than 0° C. and 10° C. or less).

In addition, in order to produce a modified hyaluronic acid having a low molecular weight (for example, having a molecular weight of less than 800,000) and a high carboxymethylation ratio (for example, 60% or more, preferably 60% or more and 200% or less), which is the second example to be described below, the reaction is carried out at a reaction liquid temperature of preferably 10° C. or more (for example, 10° C. or more and 35° C. or less, preferably 15° C. or more, more preferably 20° C. or more, still more preferably room temperature).

<Reaction Time>

In the reaction, typically, the reaction time is preferably 30 minutes or more and 100 hours or less, more preferably 60 minutes or more and 60 hours or less because carboxylation can proceed smoothly and a reduction in molecular weight can be suppressed.

First Production Example

According to the production method according to the embodiment, a modified hyaluronic acid having a molecular weight of 800,000 or more can be easily obtained. That is, according to the production method according to the embodiment, a modified hyaluronic acid having a high molecular weight and a high degree of whiteness can be easily obtained.

In this case, the modified hyaluronic acid to be obtained may have a carboxymethylation ratio of 5% or more and 200% or less.

Second Production Example

In the production method according to the embodiment, a modified hyaluronic acid having a molecular weight of 4,000 or more and less than 800,000 can be easily obtained.

In this case, the modified hyaluronic acid to be obtained may have a carboxymethylation ratio of 60% or more and 200% or less. That is, according to the production method of the embodiment, a modified hyaluronic acid having a relatively low molecular weight of 4,000 or more and less than 800,000, a high carboxymethylation ratio of 60% or more and 200% or less, and a high degree of whiteness can be easily obtained.

[Carboxymethyl-Group-Containing Modified Hyaluronic Acid and/or Salt Thereof]

<Molecular Weight>

The carboxymethyl-group-containing modified hyaluronic acid and/or the salt thereof (modified hyaluronic acid) according to the embodiment has a molecular weight of 4,000 or more and 2,000,000 or less. In the present invention, the molecular weight of the carboxymethyl-group-containing modified hyaluronic acid and/or the salt thereof can be measured by the following method.

A plurality of (purified) hyaluronic acids (standard substances) having known molecular weights are subjected to liquid chromatography analysis using a gel filtration column to prepare a calibration curve based on retention times of the substances. In the same manner as above, a modified hyaluronic acid to be measured is subjected to liquid chromatography analysis to determine a molecular weight of the modified hyaluronic acid using the calibration curve. Thus, the molecular weight of the modified hyaluronic acid can be determined.

For example, Waters Alliance 2690 HPLC Separations Module (manufactured by Waters), Waters Alliance 2695 HPLC Separations Module (manufactured by Waters), and 1200 Series (manufactured by Agilent Technologies) are given as a liquid chromatography analyzing apparatus that may be used for the liquid chromatography analysis. In addition, as a column that may be used for the liquid chromatography analysis, there are given, for example, columns for ligand exchange chromatography (ligand exchange mode and size exclusion mode) available under the model names "SUGAR KS-801", "SUGAR KS-802", "SUGAR KS-803", "SUGAR KS-804", "SUGAR KS-805", "SUGAR KS-806", and "SUGAR KS-807" from Shodex and a size exclusion chromatography column available under the model name "TSKgel GMPW" from Tosoh Corporation.

<Carboxymethylation Ratio>

In the present invention, the carboxymethylation ratio of the modified hyaluronic acid is represented as a ratio (%) of an integrated value of peaks (appearing in a range of 3.8 ppm or more and 4.2 ppm or less), in $^1$H-NMR spectra, indicating protons of a methylene group ($-CH_2-$) in a group represented by $-CH_2-CO_2H$ and/or $-CH_2-CO_2^-$ to an integrated value of peaks (appearing at about 2 ppm) indicating protons of a methyl group ($-CH_3$) in an N-acetyl group that is bonded to a hyaluronic acid skeleton at a C-2 position.

In addition, the modified hyaluronic acid according to the embodiment may have a carboxymethylation ratio of 5% or more and 200% or less and has a carboxymethylation ratio of preferably 10% or more and 200% or less, more preferably 50% or more and 200% or less, still more preferably 60% or more and 200% or less, particularly preferably 70% or more and 200% or less because the modified hyaluronic acid has a high water retention ability and a suppressed viscosity compared to a hyaluronic acid having a similar molecular weight.

The modified hyaluronic acid according to the embodiment has a carboxymethylation ratio of 5% or more and 200% or less, and hence has a low viscosity compared to a hyaluronic acid having a similar molecular weight. Therefore, the modified hyaluronic acid can be used as, for example, an ingredient of pharmaceuticals, cosmetics, and foods.

<Kinetic Viscosity>

The modified hyaluronic acid according to the embodiment has a kinetic viscosity of 1 mm$^2$/s or more and 200 mm$^2$/s or less. The kinetic viscosity of the modified hyaluronic acid according to the embodiment can be measured using an Ubbelohde viscometer (manufactured by Sibata Scientific Technology Ltd.). In this case, an Ubbelohde viscometer having such a coefficient that the falling time is from 200 seconds to 1,000 seconds is selected. The kinetic viscosity is measured in a thermostat bath at 30° C. while a constant temperature is maintained. The kinetic viscosity (unit: $mm^2/s$) can be calculated by multiplying the falling time (sec) of the aqueous solution measured using the Ubbelohde viscometer by the coefficient of the Ubbelohde viscometer.

The modified hyaluronic acid according to the embodiment has a small kinetic viscosity compared to a hyaluronic acid and/or a salt thereof having a similar molecular weight, and hence the modified hyaluronic acid has less stickiness, a good feeling of touch (light feeling), and a good texture.

<Hue>

When the modified hyaluronic acid according to the embodiment is used in, for example, cosmetics, food compositions, and pharmaceuticals, the modified hyaluronic acid according to the embodiment preferably has a high degree of lightness and a low degree of yellowness because such modified hyaluronic acid does not affect the color of a product.

The modified hyaluronic acid according to the embodiment has a b value indicating the hue of a color (hereinafter sometimes referred to simply as "b value") of 5 or less, preferably 4 or less, more preferably 3 or less, and has a b value of preferably 0 or more.

The b value is a value specifying the hue of the color of a substance. As the b value becomes larger, the degree of yellowness becomes higher. In contrast, as the b value becomes smaller, the degree of blueness becomes higher.

In addition, the modified hyaluronic acid according to the embodiment may have an L value indicating lightness of a color (hereinafter sometimes referred to simply as "L value") of 90 or more (90 or more and 100 or less), and has an L value of preferably 92 or more, more preferably 93 or more.

The L value is a value specifying the lightness of the color of a substance, and is indicated by a numerical value between 0 and 100. An L value of 100 indicates the brightest state (completely white), and an L value of 0 indicates the darkest state (completely black).

The b value and the L value may each be indicated by Lab chromaticity coordinates according to a color difference indication method specified in JIS Z 8730. In addition, the b value and the L value may each be measured using a commercially-available color difference meter. In the present invention, the b value and the L value of the modified hyaluronic acid in a solid state are measured.

The b value and the L value of the modified hyaluronic acid according to the embodiment may each be measured with, for example, a color difference meter (trade name "Color And Color Difference Meter Model 1001 DP" manufactured by Nippon Denshoku Industries Co., Ltd.) having a 10 φ lens mounted thereon and having a glass cell charged with 1 g or more of a measurement sample.

When the modified hyaluronic acid according to the embodiment has a b value measured with a color difference meter of 5 or less (further, an L value of 90 or more), the modified hyaluronic acid can be used as a raw material for cosmetics, foods, and pharmaceuticals without further requiring a purification step.

First Example (High-Molecular-Weight Product)

(Molecular Weight and Kinetic Viscosity)

A first example of the modified hyaluronic acid according to the embodiment (in the present invention, sometimes referred to as "high-molecular-weight product") has a carboxymethylation ratio of 5% or more and 200% or less (preferably 10% or more, desirably 40% or more or 50% or more, more preferably 60% or more, still more preferably 70% or more), and a molecular weight of 800,000 or more (preferably 800,000 or more and 2,000,000 or less). In this case, the first example may have a kinetic viscosity of 30 $mm^2/s$ or more and 200 $mm^2/s$ or less (preferably 50 $mm^2/s$ or more and 200 $mm^2/s$ or less).

The modified hyaluronic acid of the first example has a molecular weight of 800,000 or more and a carboxymethylation ratio of 5% or more and 200% or less. Therefore, the modified hyaluronic acid has a high molecular weight but has a low viscosity compared to a hyaluronic acid having a similar molecular weight, and hence has a good feeling of touch when used as, for example, an ingredient of pharmaceuticals or cosmetics.

A hyaluronic acid having a molecular weight of 800,000 or more has a high viscosity compared to a hyaluronic acid having a lower molecular weight. Therefore, when the hyaluronic acid is used as, for example, an ingredient of pharmaceuticals and cosmetics, the products may provide a sticky feeling when used at a high concentration. On the other hand, the modified hyaluronic acid of the first example has a molecular weight of 800,000 or more and a carboxymethylation ratio of 5% or more and 200% or less, and hence has a low viscosity compared to a hyaluronic acid having a similar molecular weight though the molecular weight is as high as 800,000 or more. Accordingly, when the modified hyaluronic acid is used as, for example, an ingredient of pharmaceuticals and cosmetics, the products have little stickiness, a good feeling of touch (light feeling), an excellent texture, and a high degree of whiteness.

Second Example (Low-Molecular-Weight Product)

(Molecular Weight and Kinetic Viscosity)

A second example of the modified hyaluronic acid according to the embodiment (in the present invention, sometimes referred to as "low-molecular-weight product") has a carboxymethylation ratio of 60% or more and 200% or less (preferably 70% or more and 200% or less) and a molecular weight of 4,000 or more and less than 800,000. In this case, the second example may have a kinetic viscosity of 1 $mm^2/s$ or more and 30 $mm^2/s$ or less (preferably 10 $mm^2/s$ or more and 29 $mm^2/s$ or less).

The modified hyaluronic acid of the second example has a molecular weight of 4,000 or more and less than 800,000 and a carboxymethylation ratio of 60% or more and 200% or less, and hence has a low viscosity compared to a hyaluronic acid having a similar molecular weight. Therefore, when the modified hyaluronic acid is used as an ingredient of, for example, pharmaceuticals and cosmetics, the products have a good feeling of touch, an excellent texture, and a high degree of whiteness.

<Conversion of Salt>

A method of converting the carboxymethyl-group-containing modified hyaluronic acid according to the embodiment into a salt thereof and a method of converting the salt of the carboxymethyl-group-containing modified hyaluronic acid according to the embodiment into the modified hyaluronic acid are not particularly limited, but may be done using a known method.

As an example of the method of converting the carboxymethyl-group-containing modified hyaluronic acid according to the embodiment into a salt thereof, there is given, for example, a method involving treating the carboxymethyl-group-containing modified hyaluronic acid with an alkaline aqueous solution (e.g., aqueous solution of sodium hydroxide, potassium hydroxide, calcium hydroxide, magnesium hydroxide, ammonium hydroxide, or the like). In addition, as examples of the method of converting the salt of the carboxymethyl-group-containing modified hyaluronic acid according to the embodiment into the modified hyaluronic acid, there are given, for example, a method involving treating the salt of the carboxymethyl-group-containing modified hyaluronic acid with an acidic aqueous solution (e.g., aqueous solution of hydrochloric acid, sulfuric acid, nitric acid, phosphoric acid, or the like) and a method involving using an acidic cation-exchange resin.

<Application>

The modified hyaluronic acid according to the embodiment has a high water retention effect resulting from the carboxyl group constituting the carboxymethyl group. Therefore, the modified hyaluronic acid has a high water retention effect in living tissues, such as skin. The modified hyaluronic acid according to the embodiment may be ingested by being applied onto or brought into contact with the surface of living tissues, and especially, the modified hyaluronic acid is preferably applied onto or brought into contact with skin on a face, arm, finger, foot, or joint.

The modified hyaluronic acid according to the embodiment has a low viscosity compared to a hyaluronic acid having a similar molecular weight resulting from the carboxyl group constituting the carboxymethyl group. Therefore, when the modified hyaluronic acid is used in, for example, a cosmetic, the product has less stickiness and a good feeling of touch (light feeling). Accordingly, the modified hyaluronic acid can be used as an ingredient of a cosmetic. In addition, the modified hyaluronic acid according to the embodiment is excellent in water solubility, and hence can be used in, for example, various water-containing products.

Alternatively, the modified hyaluronic acid according to the embodiment may be orally ingested. Accordingly, the modified hyaluronic acid according to the embodiment can be used as, for example, an ingredient of pharmaceuticals and foods.

[Action and Effect]

<Known Technology (Method of Producing Carboxymethylated Cellulose)>

To describe the action and effect of the production method according to the embodiment, first, a known method of producing carboxymethylated cellulose is described.

Carboxymethylcellulose (hereinafter sometimes referred to as "CMC") is widely utilized as, for example, an emulsifier or a thickener. The CMC is industrially produced by treating cellulose with a large volume of alkaline water to prepare alkali cellulose, dispersing the alkali cellulose in a water-containing organic solvent, and subjecting the alkali cellulose to a reaction with a monohaloacetic acid (JP 2000-34301 A).

However, when a hyaluronic acid is subjected to carboxymethylation by the above-mentioned method, carboxymethylation of the hyaluronic acid cannot sufficiently proceed. This is probably because the hyaluronic acid is not sufficiently dissolved in the water-containing organic solvent.

<Action and Effect>

(Method of Producing Modified Hyaluronic Acid)

(1) Prevention of Browning

According to the production method according to the embodiment, which includes the step of subjecting, in a water-containing solvent having a temperature of 30° C. or less, a dissolved raw material hyaluronic acid and/or a salt thereof to a reaction with a haloacetic acid and/or a salt thereof, a modified hyaluronic acid having a high degree of whiteness (for example, having a b value of 5 or less) can be easily obtained.

More specifically, according to the production method according to the embodiment, the hyaluronic acid and/or the salt thereof can be subjected to a reaction with the haloacetic acid and/or the salt thereof in a state in which at least part of the raw material hyaluronic acid and/or the salt thereof and the haloacetic acid and/or the salt thereof are dissolved in the reaction liquid (liquid mixture). Therefore, in the reaction liquid, the raw material hyaluronic acid and/or the salt thereof is highly reactive with the haloacetic acid and/or the salt thereof, and hence carboxymethylation proceeds smoothly. Thus, browning of the modified hyaluronic acid to be obtained can be prevented, and hence a modified hyaluronic acid having a high degree of whiteness can be easily obtained.

Therefore, according to the production method according to the embodiment, a modified hyaluronic acid having a high degree of whiteness can be easily obtained without general purification, such as treatment with activated carbon, and hence production efficiency is excellent. The production method according to the embodiment does not exclude performing the general purification, such as treatment with activated carbon, after the reaction step.

(2) Adjustment of Carboxymethylation Ratio

According to the production method according to the embodiment, which includes the step of subjecting, in a water-containing solvent having a temperature of 30° C. or less, a dissolved raw material hyaluronic acid and/or a salt thereof to a reaction with a haloacetic acid and/or a salt thereof, a modified hyaluronic acid having a predetermined carboxymethylation ratio can be obtained. In this method, the carboxymethylation ratio may be adjusted by, for example, appropriately selecting the concentration and kind of the haloacetic acid and/or the salt thereof, and pH, the concentration and molecular weight of the raw material hyaluronic acid and/or the salt thereof, the reaction temperature, and the reaction time.

(3) High Carboxymethylation Ratio

In particular, according to the production method according to the embodiment, as described above, a modified hyaluronic acid and/or a salt thereof having a high degree of whiteness and a high carboxymethylation ratio (for example, 50% or more) can be efficiently obtained because carboxymethylation proceeds smoothly by virtue of high reactivity between the dissolved raw material hyaluronic acid and/or the salt thereof and the haloacetic acid and/or the salt thereof in the reaction liquid.

(4) Ease of Post-Treatment

In the reaction step of the production method according to the embodiment, the generated modified hyaluronic acid is dissolved in the reaction liquid. Therefore, the generated modified hyaluronic acid can be easily separated from the haloacetic acid and/or the salt thereof serving as a reactant by adding an organic solvent, such as ethanol, to the reaction liquid to precipitate the generated modified hyaluronic acid and collecting the precipitates. Accordingly, the post-treatment can be easily performed.

(Action and Effect of Modified Hyaluronic Acid)

(1) Improvement of Water Retention Effect

The modified hyaluronic acid according to the embodiment has a carboxymethyl group, thus having more carboxyl groups compared to an unmodified hyaluronic acid and/or a salt thereof having a similar molecular weight and thus is excellent in water retention effect.

More specifically, the carboxyl group in the carboxymethyl group forms a hydrogen bond with water, and hence the water retention ability is presumed to be higher resulting from the carboxyl group.

(2) Excellent Feeling of Touch and Texture

The viscosity is presumed to be reduced by decreased tangles of the modified hyaluronic acid and/or the salt thereof in its steric structure through repulsion of negative charges of carboxyl ions ($CO_2^-$) constituting the carboxymethyl group contained in the modified hyaluronic acid according to the embodiment.

Accordingly, the modified hyaluronic acid according to the embodiment has a molecular weight of 800,000 or more and a carboxymethylation ratio of 5% or more and 200% or less or has a molecular weight of 4,000 or more and less than 800,000 and a carboxymethylation ratio of 60% or more and 200% or less, and hence the modified hyaluronic acid has a high water retention ability and a small viscosity compared to a hyaluronic acid having a similar molecular weight. Therefore, the modified hyaluronic acid according to the embodiment has less stickiness, a good feeling of touch (light feeling), and good texture, and hence can be used as, for example, an ingredient of pharmaceuticals, cosmetics, and foods.

(3) High Degree of Whiteness

The modified hyaluronic acid according to the embodiment is obtained by the production method according to the embodiment, and hence browning in the reaction is suppressed. The modified hyaluronic acid according to the embodiment has a b value indicating the hue of a color of, for example, 5 or less and a high degree of whiteness.

(4) Excellent Biocompatibility

The carboxymethyl group has high biocompatibility and low antigenicity. Therefore, as mentioned above, carboxymethylated cellulose having the carboxymethyl group is used in a wide range of applications such as cosmetics, pharmaceuticals, and foods. In addition, the hyaluronic acid is used in a wide range of applications such as cosmetics, pharmaceuticals, and foods. Therefore, the modified hyaluronic acid according to the embodiment having a part of functional groups of the hyaluronic acid carboxymethylated, has high biocompatibility and low antigenicity.

(5) Originality of Idea

A hyaluronic acid is different from cellulose, which is poor in water solubility in itself, in that the hyaluronic acid is excellent in water solubility in itself. That is, carboxymethylation of cellulose is intended to improve water solubility, while carboxymethylation of the hyaluronic acid is not intended to improve water solubility but is intended to further improve the water retention effect. Therefore, the carboxymethylation of the hyaluronic acid is completely different in idea and effect from the carboxymethylation of cellulose and is a novel and original idea.

[Cosmetic]

A cosmetic according to one embodiment of the present invention contains the modified hyaluronic acid according the above-mentioned embodiment. The content of the modified hyaluronic acid in the cosmetic according to the embodiment is, for example, 0.001 mass % or more and 5 mass % or less, and may be appropriately determined depending on the mode of use.

The aspect of the cosmetic according to the embodiment is not particularly limited, and for example, a skin cosmetic is given. When the modified hyaluronic acid according to the above-mentioned embodiment is used in a skin cosmetic, the cosmetic can give moisture to the skin and can alleviate dryness of the skin because the modified hyaluronic acid has an adequate viscosity and exhibits a high water retention effect.

Examples of the embodiment mode of the skin cosmetic according to the embodiment include a facial cleanser, a cleanser, a lotion (such as a whitening lotion), a cream (such as a banishing cream or a cold cream), a milky lotion, an essence, a pack (such as a jelly-form peel-off type pack, a paste-form wipe-out type pack, or a powder-form wash-out type pack), a cleansing, a foundation, a lip stick, a lip cream, a lip gloss, a lip liner, a rouge, a shaving lotion, an after sun lotion, a deodorant lotion, a body lotion (including a hand care lotion and a foot care lotion), a body oil, soap, and a bath additive.

The following ingredient may be further blended into the cosmetic according to the embodiment. Examples of the ingredient include: cationized polysaccharides (such as cationized hyaluronic acid, cationized hydroxyethylcellulose, cationized guar gum, cationized starch, cationized locust bean gum, cationized dextran, cationized chitosan, and cationized honey); anionic surfactants (such as an alkylbenzenesulfonic acid salt, a polyoxyalkylene alkyl ether sulfate salt, an alkyl sulfate salt, an olefin sulfonic acid salt, a fatty acid salt, and a dialkylsulfosuccinic acid salt); nonionic surfactants (such as a polyoxyethylene fatty acid ester and a polyoxyethylene hydrogenated castor oil derivative); cationic surfactants (such as an alkyltrimethylammonium salt, a dialkyldimethylammonium salt, an alkylpyridinium salt, and stearyltrimethylammonium chloride); amphoteric surfactants (such as an alkyl betaine, an alkylamidopropyl betaine, an imidazolinium betaine, egg yolk lecithin, and soybean lecithin); oil contents (such as silicone, a silicone derivative, liquid paraffin, squalane, beeswax, carnauba wax, olive oil, avocado oil, camellia oil, jojoba oil, and horse oil); moisturizers (such as sodium hyaluronate, hydrolyzed hyaluronic acid, acetylated hyaluronic acid, dimethylsilanol hyaluronate, ceramide, diphytosteryloctyldodecyl lauroylglutamate, phytoglycogen, a hydrolyzed egg shell membrane, trehalose, glycerin, atelocollagen, sorbitol, maltitol, and 1,3-butylene glycol); higher fatty acids (such as lauric acid, behenic acid, palmitic acid, stearic acid, isostearic acid, and oleic acid); higher alcohols (such as cetyl alcohol, stearyl alcohol, behenyl alcohol, isostearyl alcohol, and batyl alcohol); polyhydric alcohols (such as glycerin, diglycerin, 1,3-propanediol, propylene glycol, polyethylene glycol, and pentylene glycol); thickeners (such as cellulose ether, a carboxyvinyl polymer, xanthan gum, and dextrin palmitate); amphoteric polymer resin compounds (such as a betainized dialkylaminoalkyl acrylate copolymer); cationic polymer resin compounds (such as a cationized vinylpyrrolidone/dimethylaminoethyl methacrylate copolymer and a polydimethyldiallylammonium halide-type cationic polymer); antiseptics (such as methylparaben, ethylparaben, butylparaben, propylparaben, and phenoxyethanol); antioxidants (such as tocopherol and BHT); sequestering agents (such as an edetic acid salt and an etidronic acid salt); UV absorbers (such as a benzophenone derivative, a p-aminobenzoic acid derivative, and a methoxycinnamic acid derivative); UV reflectors (such as titanium oxide and zinc oxide); protein hydrolysates (such as a keratin peptide, a collagen peptide, a soybean peptide, a wheat peptide, a milk peptide, a silk peptide, and an egg white peptide); amino acids (such as arginine, glutamic acid, glycine, alanine, hydroxyproline, cysteine, serine, and L-theanine); natural product extracts (a *Sophora Angustifolia* root extract, a seagrass extract, a eucalyptus extract, a royal jelly extract, a rosemary extract, and a beech tree extract); other functional ingredients (coenzyme Q10, arbutin, polyquaternium-51, elastin, a platinum nanocolloid, retinol palmitate, panthenol, allantoin, sodium dilauramidoglutamide lysine, ascorbyl-magnesium phosphate, L-ascorbic acid 2-glucoside, ellagic acid, kojic acid, linoleic acid, and tranexamic acid); phospholipid polymers; perfumes; and dyes.

[Food Composition]

A food composition according to one embodiment of the present invention contains the modified hyaluronic acid according to the above-mentioned embodiment. The content of the modified hyaluronic acid in the food composition according to the embodiment is, for example, 0.001 mass % or more and 5 mass % or less, and may be appropriately determined depending on the mode of use. When the modified hyaluronic acid according to the above-mentioned embodiment is used in the food composition, the food composition has an excellent texture because the modified hyaluronic acid has a suppressed viscosity compared to a hyaluronic acid having a similar molecular weight.

The embodiment mode of the food composition containing the modified hyaluronic acid according to the embodiment is not particularly limited. Examples thereof include: overall general food, e.g., staple food, such as rice processed food and bread, dishes other than staple food, such as retort canned food, frozen food, daily dishes, and dry food, seasoning, such as mayonnaise, beverages, sweets, dessert, and liquid, gelled, or soft-capsuled supplements; and overall food for specified health use for which use of health claims is allowed.

[Pharmaceutical Composition]

A pharmaceutical composition according to one embodiment of the present invention contains the modified hyaluronic acid according to the above-mentioned embodiment. The content of the modified hyaluronic acid in the pharmaceutical composition according to the embodiment is, for example, 0.001 mass % or more and 5 mass % or less, and may be appropriately determined depending on the mode of use. When the modified hyaluronic acid according to the above-mentioned embodiment is used in the pharmaceutical composition, the pharmaceutical composition has an excellent texture because the modified hyaluronic acid has a suppressed viscosity compared to a hyaluronic acid having a similar molecular weight.

The mode of use of the pharmaceutical composition according to the embodiment is not particularly limited, and may be a powder form, a granule form, a high-concentrated liquid form, or a low-concentrated liquid form. From the viewpoint of stability of the molecular weight of the modified hyaluronic acid according to the above-mentioned embodiment, a dried form is more preferred than a liquid form.

For example, the following may be blended into the pharmaceutical composition according to the embodiment as required: an extender, a binder, a lubricant, a preservative, an antioxidant, a perfume, a sweetener, an acidulant, or an excipient. In addition, for example, the following various nutritional ingredients may also be blended: vitamins, such as vitamin C, vitamin B2, vitamin B12, and vitamin E; nutritional ingredients, such as a nucleic acid, chondroitin sulfate, and collagen; and mineral ingredients, such as iron and zinc.

EXAMPLES

The present invention is hereinafter described in more detail by way of Examples. However, the present invention is by no means limited to Examples.

Experimental Example 1: Preparation of Carboxymethyl-Group-Containing Modified Hyaluronic Acid 1.04 g of sodium hydroxide was weighed in a 30 mL sample bottle, and 8 mL of water was added thereto to dissolve sodium hydroxide. Subsequently, 2.0 g of a hyaluronic acid was added thereto and dissolved therein, and 1.52 g of sodium monochloroacetate was added thereto and dissolved therein, followed by still standing at room temperature for 48 hours. At that time, the reaction liquid had a pH of 13. After that, 80 mL of ethanol was charged into a 200 mL beaker, and the reaction liquid was added thereto while the reaction liquid was stirred, to thereby precipitate a carboxymethyl-group-containing modified hyaluronic acid. Subsequently, the precipitates were collected in a 200 mL beaker using a 400-mesh filter cloth, and 40 mL of a 10% aqueous solution of sodium chloride was added thereto to dissolve the precipitates. Further, the pH of the mixture was adjusted with an 8% aqueous solution of hydrochloric acid, and 80 mL of ethanol was added to the solution while the mixture was stirred, to thereby again precipitate a carboxymethyl-group-containing modified hyaluronic acid. The precipitates were washed three times with 100 mL of 80% aqueous ethanol, filtered under reduced pressure, and dried under reduced pressure at 55° C. for 3 hours. Thus, a Carboxymethyl-group-containing Modified Hyaluronic Acid of Experiment No. 1 was obtained.

Experimental Example 2: Preparation of Carboxymethyl-Group-Containing Modified Hyaluronic Acid Carboxymethyl-group-containing modified hyaluronic acids of Experiment Nos. 2 to 36 were obtained in the same manner as in Example 1 except that the concentration of sodium hydroxide, the usage amount of the water-containing solvent, the kind of the solvent, the kind and usage amount of the haloacetic acid and/or a salt thereof, the reaction temperature, and the reaction time were changed as shown in Table 1 and Table 2. In this example, the term "room temperature" refers to a temperature of 25° C. or more and 30° C. or less.

The results of use of sodium monochloroacetate as the haloacetic acid and/or the salt thereof are shown in Table 1, and the results of use of monobromoacetic acid as the haloacetic acid and/or the salt thereof are shown in Table 2.

All of the reaction liquids of Experiment Nos. 2 to 36 had a pH in a range of 10 or more and 14 or less.

The carboxymethyl-group-containing modified hyaluronic acids of Experiment Nos. 1 to 17, 19 to 29, and 31 to 36 were found to be white by visual observation (each had a b value of or less). On the other hand, the carboxymethyl-group-containing modified hyaluronic acids of Experiment Nos. 18 and 30 were found to turn brown by visual observation (each had a b value much larger than 5).

TABLE 1

| | | Experiment No. | | | | | | |
|---|---|---|---|---|---|---|---|---|
| | | 1 | 2 | 3 | 4 | 5 | 6 | 7 |
| Raw material hyaluronic acid | Molecular weight | 1,750,000 | 1,750,000 | 1,750,000 | 1,750,000 | 1,750,000 | 1,750,000 | 1,750,000 |
| Reaction conditions | Concentration of sodium monochloroacetate [mol/l] | 1.63 | 1.63 | 1.63 | 0.82 | 1.63 | 1.09 | 2.17 |
| | Usage amount of sodium monochloroacetate [g] | 1.52 | 1.52 | 1.52 | 0.76 | 1.52 | 1.52 | 3.04 |
| | Concentration of NaOH in reaction liquid [mol/l] | 3.25 | 1.63 | 0.81 | 0.81 | 0.813 | 3.25 | 3.25 |
| | Kind of water-soluble organic solvent | — | — | — | — | — | — | — |
| | Water-soluble organic solvent:water | 0:100 | 0:100 | 0:100 | 0:100 | 0:100 | 0:100 | 0:100 |
| | Usage amount of water-containing solvent | 8 mL | 8 mL | 8 mL | 8 mL | 8 mL | 12 mL | 12 mL |
| | Reaction temperature | Room temperature | Room temperature | 4° C. | Room temperature | Room temperature | Room temperature | Room temperature |
| | Reaction time | 48 hours | 48 hours | 48 hours | 48 hours | 48 hours | 48 hours | 48 hours |
| Carboxymethyl-group-containing modified hyaluronic acid | Molecular weight | 170,000 | 200,000 | 840,000 | 190,000 | 250,000 | 200,000 | 203,000 |
| | CM ratio | 78% | 83% | 7% | 76% | 62% | 71% | 103% |

| | | Experiment No. | | | | | |
|---|---|---|---|---|---|---|---|
| | | 8 | 9 | 10 | 11 | 12 | 13 |
| Raw material hyaluronic acid | Molecular weight | 1,750,000 | 1,750,000 | 1,750,000 | 1,750,000 | 1,750,000 | 1,750,000 |
| Reaction conditions | Concentration of sodium monochloroacetate [mol/l] | 1.63 | 1.09 | 2.17 | 1.63 | 1.63 | 1.63 |
| | Usage amount of sodium monochloroacetate [g] | 1.52 | 1.52 | 3.04 | 3.04 | 1.52 | 1.52 |
| | Concentration of NaOH in reaction liquid [mol/l] | 3.25 | 3.25 | 3.25 | 3.25 | 3.25 | 3.25 |
| | Kind of water-soluble organic solvent | — | — | — | — | — | — |
| | Water-soluble organic solvent:water | 0:100 | 0:100 | 0:100 | 0:100 | 0:100 | 0:100 |
| | Usage amount of water-containing solvent | 8 mL | 12 mL | 12 mL | 16 mL | 8 mL | 8 mL |
| | Reaction temperature | Room temperature | 4° C. | 4° C. | 4° C. | Room temperature | Room temperature |
| | Reaction time | 24 hours | 48 hours | 48 hours | 48 hours | 3 hours | 6 hours |
| Carboxymethyl-group-containing modified hyaluronic acid | Molecular weight | 250,000 | 970,000 | 1,036,000 | 1,120,000 | 940,000 | 830,000 |
| | CM ratio | 81% | 12% | 8% | 10% | 27% | 30% |

| | | Experiment No. | | | | | |
|---|---|---|---|---|---|---|---|
| | | 14 | 15 | 16 | 17 | 18 | 19 |
| Raw material hyaluronic acid | Molecular weight | 1,750,000 | 2,400,000 | 1,000,000 | 1,490,000 | 1,750,000 | 1,750,000 |
| Reaction conditions | Concentration of sodium monochloroacetate [mol/l] | 1.09 | 1.63 | 1.63 | 1.63 | 1.63 | 1.63 |
| | Usage amount of sodium monochloroacetate [g] | 1.52 | 1.52 | 1.52 | 1.52 | 1.52 | 1.52 |
| | Concentration of NaOH in reaction liquid [mol/l] | 3.25 | 0.813 | 3.25 | 3.25 | 3.25 | 3.25 |

TABLE 1-continued

|  |  |  |  |  |  |  |  |
|---|---|---|---|---|---|---|---|
|  | Kind of water-soluble organic solvent | — | — | Isopropanol | Isopropanol | — | Ethanol |
|  | Water-soluble organic solvent:water | 0:100 | 0:100 | 100:10 | 100:10 | 0:100 | 20:30 |
|  | Usage amount of water-containing solvent | 12 mL | 8 mL | 8 mL | 8 mL | 8 mL | 8 mL |
|  | Reaction temperature | 20° C. | Room temperature | Room temperature | Room temperature | 60° C. | Room temperature |
|  | Reaction time | 48 hours | 4 hours | 3 hours | 3 hours | 3 hours | 24 hours |
| Carboxymethyl-group-containing modified hyaluronic acid | Molecular weight | 380,000 | 1,760,000 | 400,000 | 470,000 | 13,000 | 890,000 |
|  | CM ratio | 65% | 24% | 54% | 29% | 46% | 26% |

TABLE 2

|  |  | Experiment No. | | | | | |
|---|---|---|---|---|---|---|---|
|  |  | 20 | 21 | 22 | 23 | 24 | 25 |
| Raw material hyaluronic acid | Molecular weight | 1,750,000 | 1,750,000 | 1,750,000 | 1,750,000 | 1,750,000 | 1,750,000 |
| Reaction conditions | Concentration of monobromoacetic acid [mol/l] | 1.63 | 1.63 | 1.09 | 2.17 | 2.17 | 2.17 |
|  | Usage amount of monobromoacetic acid [g] | 1.81 | 1.81 | 1.81 | 3.62 | 3.62 | 3.62 |
|  | Concentration of NaOH in reaction liquid [mol/l] | 3.25 | 3.25 | 3.25 | 6.5 | 6.5 | 6.5 |
|  | Kind of water-soluble organic solvent | — | — | — | — | — | — |
|  | Water-soluble organic solvent:water | 0:100 | 0:100 | 0:100 | 0:100 | 0:100 | 0:100 |
|  | Usage amount of water-containing solvent | 8 mL | 8 mL | 12 mL | 12 mL | 12 mL | 12 mL |
|  | Reaction temperature | 4° C. | 4° C. | 4° C. | 4° C. | 4° C. | 4° C. |
|  | Reaction time | 24 hours | 48 hours | 24 hours | 24 hours | 3 hours | 6 hours |
| Carboxymethyl-group-containing modified hyaluronic acid | Molecular weight | 1,270,000 | 1,160,000 | 1,060,000 | 1,260,000 | 1,590,000 | 1,290,000 |
|  | CM ratio | 78% | 80% | 67% | 99% | 61% | 68% |

|  |  | Experiment No. | | | | | |
|---|---|---|---|---|---|---|---|
|  |  | 26 | 27 | 28 | 29 | 30 | 31 |
| Raw material hyaluronic acid | Molecular weight | 1,750,000 | 300,000 | 1,750,000 | 1,750,000 | 1,750,000 | 1,750,000 |
| Reaction conditions | Concentration of monobromoacetic acid [mol/l] | 2.17 | 2.17 | 1.63 | 1.63 | 1.37 | 1.09 |
|  | Usage amount of monobromoacetic acid [g] | 3.62 | 3.62 | 1.81 | 1.81 | 1.52 | 1.81 |
|  | Concentration of NaOH in reaction liquid [mol/l] | 6.5 | 6.5 | 3.25 | 3.25 | 3.25 | 3.25 |
|  | Kind of water-soluble organic solvent | — | — | — | — | — | Ethanol |
|  | Water-soluble organic solvent:water | 0:100 | 0:100 | 0:100 | 0:100 | 0:100 | 20:80 |

TABLE 2-continued

| | | Usage amount of water-containing solvent | 12 mL | 12 mL | 8 mL | 8mL | 8 mL | 12 mL |
|---|---|---|---|---|---|---|---|---|
| | | Reaction temperature | 4° C. | 4° C. | Room temperature | Room temperture | 60° C. | 4° C. |
| | | Reaction time | 16 hours | 16 hours | 24 hours | 48 hours | 3 hours | 24 hours |
| Carboxymethyl-group-containing modified hyaluronic acid | | Molecular weight | 1,480,000 | 380,000 | 340,000 | 180,000 | 70,000 | 1,650,000 |
| | | CM ratio | 88% | 79% | 98% | 92% | 54% | 65% |

| | | | Experiment No. | | | | |
|---|---|---|---|---|---|---|---|
| | | | 32 | 33 | 34 | 35 | 36 |
| Raw material hyaluronic acid | | Molecular weight | 1,750,000 | 1,750,000 | 2,400,000 | 2,400,00 | 2,400,000 |
| Reaction conditions | | Concentration of monobromoacetic acid [mol/l] | 1.09 | 1.09 | 1.09 | 1.09 | 1.09 |
| | | Usage amount of monobromoacetic acid [g] | 1.81 | 1.81 | 1.81 | 1.81 | 1.81 |
| | | Concentration of NaOH in reaction liquid [mol/l] | 3.25 | 3.25 | 3.25 | 3.25 | 3.25 |
| | | Kind of water-soluble organic solvent | Ethanol | Ethanol | — | — | — |
| | | Water-soluble organic solvent:water | 30:70 | 50:50 | 0:100 | 0:100 | 0:100 |
| | | Usage amount of water-containing solvent | 12 mL | 12 mL | 12 mL | 12 mL | 12 mL |
| | | Reaction temperature | 4° C. | 4° C. | 4° C. | 4° C. | 4° C. |
| | | Reaction time | 24 hours | 24 hours | 4 hours | 2 hours | 1 hour |
| Carboxymethyl-group-containing modified hyaluronic acid | | Molecular weight | 1,510,000 | 1,410,000 | 1,260,000 | 1,660,000 | 2,210,000 |
| | | CM ratio | 56% | 55% | 77% | 63% | 41% |

The molecular weights of the carboxymethyl-group-containing modified hyaluronic acids of Experiment Nos. 1 to 36 were measured by the method described in the above-mentioned embodiment. In addition, the kinetic viscosities of the carboxymethyl-group-containing modified hyaluronic acids of Experiment Nos. 2, 20, 21, 23, 27, and 36 were measured by the method described in the above-mentioned embodiment and were found to be 3.49 mm$^2$/s, 91.8 mm$^2$/s, 54.7 mm$^2$/s, mm$^2$/s, 9.69 mm$^2$/s, and 121.10 mm$^2$/s, respectively. The carboxymethylation ratios of the carboxymethyl-group-containing modified hyaluronic acids of Experiment Nos. 1 to 36 were determined by the following method based on integrated values of $^1$H-NMR spectra.

(Sample Preparation)

7 mg of a sample and 1 mg of an internal standard substance sodium 4,4-dimethyl-4-silapentanesulfonate (DSS) were dissolved in 0.7 mL of deuterium oxide. The resultant solution was transferred into an NMR sample tube, and the tube was capped.

(Measurement Condition)

Apparatus: Varian NMR system, model: 400NB (Varian Technologies Japan, Ltd.)

Observation frequency: 400 MHz

Temperature: 30° C.

Standard: DSS (0 ppm)

Number of transients: 64

(Analysis Method)

Peaks of N-acetyl groups (CH$_3$) of the hyaluronic acid observed at about 2.0 ppm in $^1$H-NMR spectra and peaks of methylene groups (—CH$_2$—) of the carboxymethyl groups observed in a range of 3.8 ppm or more and 4.2 ppm or less were integrated. The number of the carboxymethyl groups bonded to each disaccharide repeating unit of hyaluronic acid constituting the modified hyaluronic acid was determined from the integrated values by the following expression to determine a carboxymethylation ratio (CM ratio).

CM ratio=(Integrated value of peaks observed in a range of 3.8 ppm or more and 4.2 ppm or less/ 2)/(Integrated value of peaks observed at 2.0 ppm/3)

As shown in Table 1 and Table 2, it can be understood that, according to the carboxymethyl-group-containing modified hyaluronic acids of Experiment Nos. 1 to 15, 19 to 29, and 31 to 36, a modified hyaluronic acid having a high degree of whiteness and a high carboxymethylation ratio can be obtained by an easy method including a step of subjecting, in a water-containing solvent having a temperature of 30° C. or less, a dissolved raw material hyaluronic acid and/or a salt thereof to a reaction with a haloacetic acid and/or a salt thereof, the water-containing solvent being water or a liquid mixture of the water-soluble organic solvent and water, the ratio of the water-soluble organic solvent in the liquid mixture being 60 v/v % or less.

It can be understood that, of those, like Experiment Nos. 20 to 26 and 31 to 36, when the reaction is performed using monobromoacetic acid as the haloacetic acid and/or the salt thereof in a water-containing solvent having a temperature of 10° C. or less, a modified hyaluronic acid having a high degree of whiteness, a high molecular weight (800,000 or more), and a high carboxymethylation ratio (40% or more, preferably 50% or more) can be obtained. It can be understood that the modified hyaluronic acid has a water retention ability and a small viscosity compared to a hyaluronic acid having a similar molecular weight. Accordingly, the carboxymethyl-group-containing modified hyaluronic acid and/or a salt thereof of the present invention has less stickiness, a good feeling of touch, less stickiness, and a good feeling of hand touch (light feeling of touch) and good texture, and hence can be used as, for example, an ingredient of pharmaceuticals, cosmetics, and foods.

In addition, it can be understood that, like Experiment Nos. 27 to 29, when the reaction is performed using monobromoacetic acid as the haloacetic acid and/or the salt thereof in a water-containing solvent having a temperature of 30° C. or less, a modified hyaluronic acid having a high degree of whiteness, a molecular weight of 4,000 or more and less than 800,000, and a high carboxymethylation ratio (60% or more) can be obtained.

Further, it can be understood that, like Experiment Nos. 3, 9 to 13, 15, and 19, when the molecular weight of the raw material hyaluronic acid and/or the salt thereof, the reaction temperature, the reaction time, and the amounts of sodium monochloroacetate and sodium hydroxide to be used are adjusted in the reaction using sodium monochloroacetate as the haloacetic acid and/or the salt thereof in the water-containing solvent having a temperature of 30° C. or less, a modified hyaluronic acid having a high degree of whiteness, a high molecular weight (800,000 or more), and a carboxymethylation ratio of 5% or more and 200% or less can be obtained.

Further, it can be understood that, like Experiment Nos. 1, 2, 4 to 8, and 14, when the molecular weight of the raw material hyaluronic acid and/or the salt thereof, the reaction temperature, the reaction time, and the amounts of sodium monochloroacetate and sodium hydroxide to be used are adjusted in the reaction using sodium monochloroacetate as the haloacetic acid and/or the salt thereof in the water-containing solvent having a temperature of 30° C. or less, a modified hyaluronic acid having a high degree of whiteness, a molecular weight of 4,000 or more and less than 800,000, and a high carboxymethylation ratio (60% or more and 200% or less) can be obtained.

On the other hand, in Experiment Nos. 16 and 17, a modified hyaluronic acid having a relatively low molecular weight (less than 800,000) and a high carboxymethylation ratio (60% or more and 200% or less) could not be obtained.

In Experiment Nos. 16 and 17, the majority of the hyaluronic acid used was not dissolved in the water-containing solvent to separate the reaction liquid into two phases because the ratio of the water-soluble organic solvent in the water-containing solvent used in the reaction was more than 60 v/v %. Therefore, in Experiment Nos. 16 and 17, after completion of the reaction, it was necessary to remove sodium monochloroacetate used in the reaction by dissolving the reaction product once in water and forming precipitates to purify the product, and such post-treatment was cumbersome.

On the other hand, in Experiment Nos. 1 to 15, 18, 20 to 29, and 31 to 36, the generated carboxymethyl-group-containing modified hyaluronic acid was dissolved in the reaction liquid. Therefore, the generated carboxymethyl-group-containing modified hyaluronic acid was able to be separated easily from the haloacetic acid and/or the salt thereof used as a reactant by adding ethanol to the reaction liquid to precipitate the generated carboxymethyl-group-containing modified hyaluronic acid and collecting the precipitates, and such post-treatment was easy.

Test Example 1: Water Retention Ability Test

A weighing bottle was placed in a vacuum dryer together with 10 g of phosphorus (V) oxide, and dried under reduced pressure at 60° C. for 30 minutes. The dried weighing bottle was cooled in a desiccator, and then the weight of the empty weighing bottle was measured. Subsequently, 1.0 g of 1.0% solutions of the carboxymethyl-group-containing modified hyaluronic acids of Experiment Nos. 6, 12, and 23 were weighed. In addition, three kinds of hyaluronic acids (manufactured by Kewpie Corporation) having the same or similar molecular weights (200,000, 900,000, 1,200,000) as or to those of the carboxymethyl-group-containing modified hyaluronic acids of Experiment Nos. 6, 12, and 23 were weighed in weighing bottles by the same treatment as above. Next, the weighing bottles were placed in the desiccator including silica gel and maintained in an incubator at 35° C. for 22.5 hours, and the mass of each sample was measured. Based on the following expression, water retention rates (%) were calculated.

Water retention rate (%)={(Mass of sample before placement in incubator)−(Mass of sample after 22.5 hours)}/(Mass of sample before placement in incubator)×100(%)

The measurement results of the water retention rates of the modified hyaluronic acids and the hyaluronic acids are shown in FIG. 1. In the graph of FIG. 1, the left bars each indicate a water retention rate of a hyaluronic acid (unmodified), and the right bars each indicate a water retention rate of a carboxymethyl-group-containing modified hyaluronic acid. The bars are shown in pairs by molecular weight.

According to FIG. 1, it can be understood that the carboxymethyl-group-containing modified hyaluronic acids of the present invention have high water retention rates compared to a hyaluronic acid having a similar molecular weight.

Test Example 2: Sensory Test

The modified hyaluronic acid of Experiment No. 21 was subjected to sensory evaluation on a viscosity (visual observation) and a feeling of touch. In the sensory evaluation, a hyaluronic acid having a molecular weight of 800,000 and a hyaluronic acid having a molecular weight of 1,170,000 (manufactured by Kewpie Corporation) were used as controls.

Figure 2:
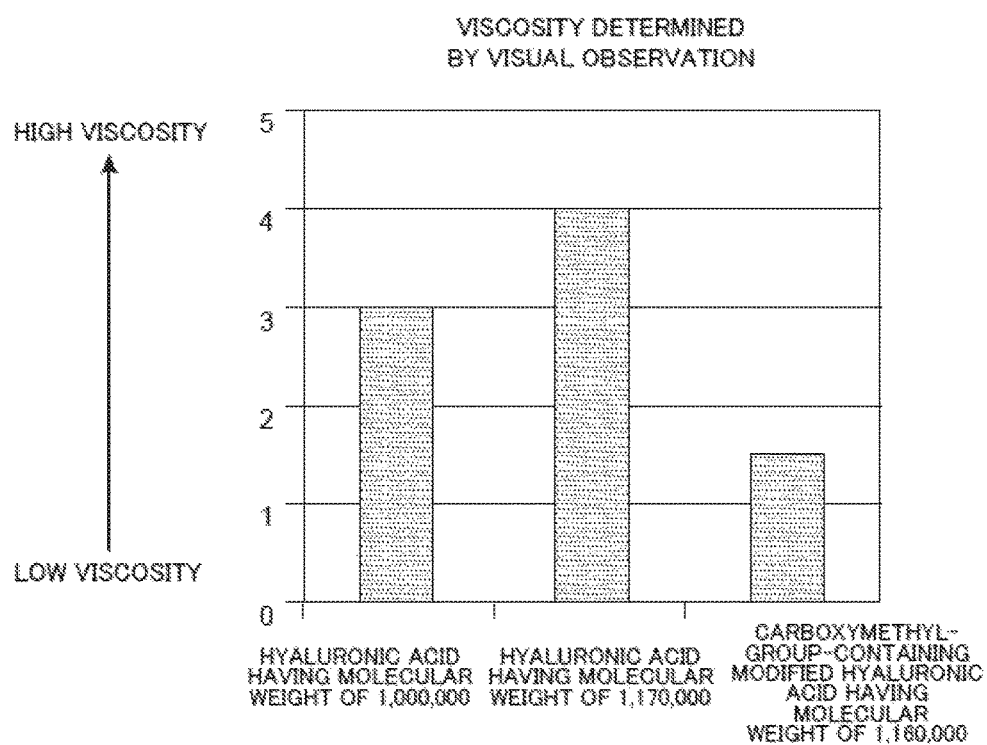
FIG. 2 is a graph for showing results of a sensory test on a viscosity of a carboxymethyl-group-containing modified hyaluronic acid and/or a salt thereof according to one example of the present invention.
Figure 3:
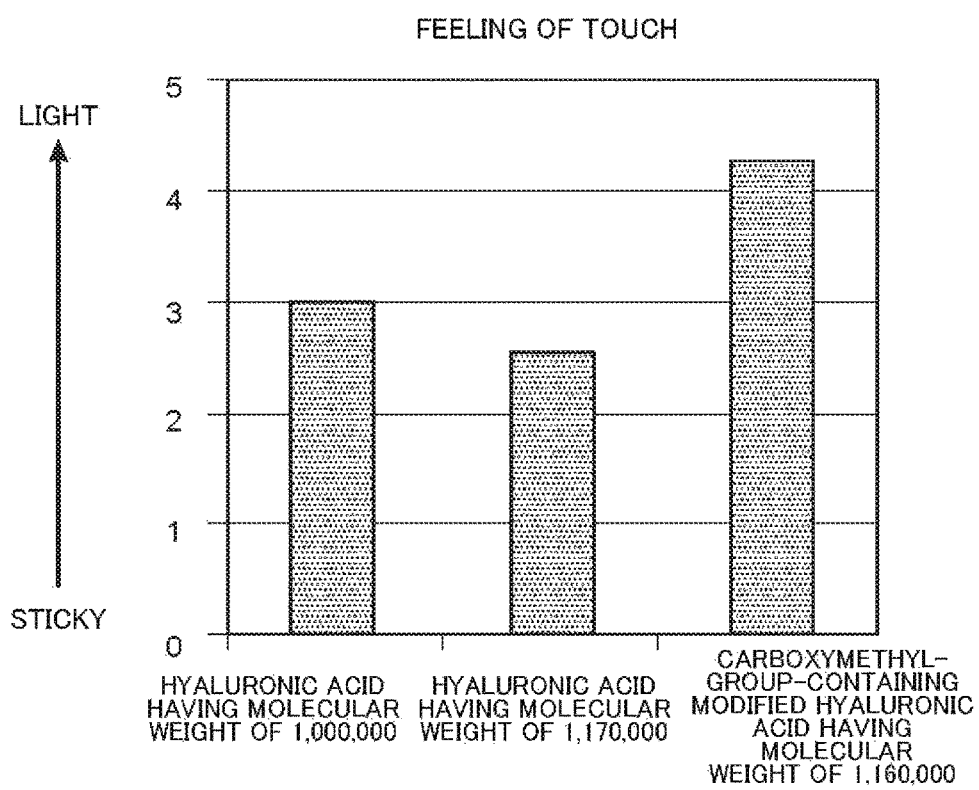
FIG. 3 is a graph for showing results of a sensory test on a feeling of touch of a carboxymethyl-group-containing modified hyaluronic acid and/or a salt thereof according to one example of the present invention.

The samples were evaluated by six adult panelists (five men and one woman) according to the following criteria based on the viscosity (visual observation) and the feeling of touch of the hyaluronic acid having a molecular weight of 800,000 defined as 3 points. Averages of the results of the evaluations by the six panelists are shown in FIG. 2 and FIG. 3.

Aqueous solutions containing the respective samples at a concentration of 1% were used as evaluation samples. In addition, the feeling of touch was evaluated by applying each aqueous solution to the upper arm.

(Evaluation Criteria)

Viscosity (visual observation) . . . 5 points (high viscosity), 4 points (slightly high viscosity), 3 points (normal viscosity), 2 points (slightly low viscosity), 1 point (low viscosity)

Feeling of touch . . . 5 points (light feeling), 4 points (less sticky and relatively light feeling), 3 points (sticky feeling), 2 points (significant sticky feeling), 1 point (extremely sticky feeling)

According to FIG. 2 and FIG. 3, it can be understood that the carboxymethyl-group-containing modified hyaluronic acid of the present invention has less stickiness and a light feeling and has an external appearance of a low viscosity compared to a hyaluronic acid having a similar molecular weight.

Test Example 3: Whiteness

The b values and the L values of the carboxymethyl-group-containing modified hyaluronic acids of Experiment Nos. 18, 21, and 30 were measured with a color difference meter (trade name "Color And Color Difference Meter Model 1001 DP" manufactured by Nippon Denshoku Industries Co., Ltd.) in which a 10 φ lens was installed and a glass cell was charged with 1 g or more of a measurement sample. The results are shown in Table 3.

TABLE 3

| Experiment No. of carboxymethyl-group-containing modified hyaluronic acid | b value | L value |
| --- | --- | --- |
| 18 | 18.64 | 82.67 |
| 21 | 1.60 | 95.29 |
| 30 | 8.93 | 91.23 |

The carboxymethyl-group-containing modified hyaluronic acid of Experiment No. 21, which is obtained by a reaction at 30° C. or less, is found to be white by visual observation, and has a b value indicating the hue of a color of 5 or less. Thus, the carboxymethyl-group-containing modified hyaluronic acid of Experiment No. 21 can be understood as having a high degree of whiteness.

On the other hand, the carboxymethyl-group-containing modified hyaluronic acids of Experiment Nos. 18 and 30, which are each obtained by a reaction at a temperature more than 30° C., are found to turn brown by visual observation, and have b values indicating the hue of a color of much higher than 5. Thus, the carboxymethyl-group-containing modified hyaluronic acids of Experiment Nos. 18 and 30 can be understood as having low degrees of whiteness.

Formulation Example 1: Lotion

In this formulation example, a lotion containing the carboxymethyl-group-containing modified hyaluronic acid obtained in Experimental Example 1 was prepared according to the following formulation.

| | |
| --- | --- |
| Carboxymethyl-group-containing modified hyaluronic acid (Experimental Example 1) | 0.2% |
| Sodium hyaluronate | 0.1% |
| Hydrolyzed hyaluronic acid | 0.1% |
| C12-13 alkyl glyceryl hydrolyzed hyaluronate | 0.1% |

-continued

| | |
| --- | --- |
| Collagen peptide | 0.1% |
| 1,3-Butylene glycol | 5.0% |
| Glycerin | 3.0% |
| Isostearyl alcohol | 0.1% |
| Tocopherol acetate | 0.1% |
| POE(20) sorbitan monolauric acid ester | 0.5% |
| POE(15) lauryl alcohol ether | 0.5% |
| Zinc pyrrolidonecarboxylate | 0.1% |
| Ethylparaben | 0.1% |
| Methylparaben | 0.15% |
| Ethanol | 5.0% |
| Perfume | q.s. |
| Purified water | balance |

Formulation Example 2: Milky Lotion

In this formulation example, a milky lotion containing the carboxymethyl-group-containing modified hyaluronic acid obtained in Experimental Example 1 was prepared according to the following formulation.

| | |
| --- | --- |
| Carboxymethyl-group-containing modified hyaluronic acid (Experimental Example 1) | 0.3% |
| Pentylene glycol | 5.0% |
| Glycerin | 3.0% |
| Squalane | 5.0% |
| Stearic acid | 0.5% |
| Stearyl alcohol | 2.0% |
| Vaseline | 4.0% |
| Sorbitan stearate | 1.0% |
| POE(10) monostearic acid ester | 1.0% |
| Carboxyvinyl polymer | 0.5% |
| Polyquaternium-51 | 0.1% |
| Methylparaben | 0.15% |
| Propylparaben | 0.1% |
| Potassium hydroxide | 0.1% |
| BHT | 0.02% |
| Disodium EDTA | 0.02% |
| Perfume | q.s. |
| Purified water | balance |

Formulation Example 3: Cream

In this formulation example, a cream (emollient cream) containing the carboxymethyl-group-containing modified hyaluronic acid obtained in Experimental Example 2 was prepared according to the following formulation.

| | |
| --- | --- |
| Carboxymethyl-group-containing modified hyaluronic acid (Experimental Example 2) | 0.5% |
| Polyethylene glycol | 4.0% |
| 1,3-Propanediol | 6.0% |
| Squalane | 11.0% |
| Dimethicone | 1.0% |
| Cetanol | 6.0% |
| Stearic acid | 2.0% |
| Hydrogenated coco-glycerides | 4.0% |
| Tricaprylin | 8.0% |
| Glycerin monostearate | 3.0% |
| POE(20) cetyl alcohol ether | 2.0% |
| Coenzyme Q10 | 0.03% |
| Ceramide | 0.1% |
| Sodium dilauramidoglutamide lysine | 0.1% |
| Disodium EDTA | 0.02% |
| Propylparaben | 0.1% |
| Methylparaben | 0.15% |
| Perfume | q.s. |
| Purified water | balance |

Formulation Example 4: Essence

In this formulation example, an essence (whitening/moisturizing essence) containing the carboxymethyl-group-containing modified hyaluronic acid obtained in Experimental Example 2 was prepared according to the following formulation.

| | |
|---|---|
| Carboxymethyl-group-containing modified hyaluronic acid (Experimental Example 2) | 0.8% |
| Sodium hyaluronate | 0.2% |
| Hydrolyzed hyaluronic acid | 0.1% |
| 1,3-Butylene glycol | 5.0% |
| Glycerin | 1.5% |
| POE sorbitan monostearic acid ester | 1.0% |
| Sorbitan monostearic acid ester | 0.5% |
| Xanthan gum | 0.2% |
| Sodium alginate | 0.2% |
| Carboxyvinyl polymer | 0.2% |
| Potassium hydroxide | 0.1% |
| Olive oil | 0.2% |
| Tocopherol | 0.1% |
| Disodium EDTA | 0.02% |
| Arginine | 0.15% |
| Dipotassium glycyrrhizate | 0.05% |
| Arbutin | 0.2% |
| Retinol palmitate | 0.2% |
| Sophora Angustifolia root extract | 0.2% |
| Seaweed extract | 0.2% |
| Tranexamic acid | 0.1% |
| Elastin | 0.1% |
| Collagen | 0.1% |
| Magnesium ascorbate phosphate | 0.1% |
| Sodium citrate | 1.0% |
| Citric acid | 0.1% |
| Propylparaben | 0.1% |
| Methylparaben | 0.15% |
| Perfume | q.s. |
| Purified water | balance |

Formulation Example 5: Essence Pack

In this formulation example, an essence pack (paste-form peel-off type pack) containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.5% |
| Polyvinyl acetate emulsion | 17.0% |
| Polyvinyl alcohol | 11.0% |
| Sorbitol | 5.0% |
| Polyethylene glycol 400 | 5.0% |
| Squalane | 2.5% |
| POE sorbitan monostearic acid ester | 1.0% |
| Titanium oxide | 4.0% |
| Talc | 8.0% |
| Ethanol | 8.0% |
| Methylparaben | 0.15% |
| Perfume | q.s. |
| Purified water | balance |

Formulation Example 6: Facial Cleanser

In this formulation example, a facial cleanser (cleansing foam) containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.2% |
| Cationized hyaluronic acid (Hyaloveil, manufactured by Kewpie Corporation) | 0.1% |
| Glycerin | 10.0% |
| Polyethylene glycol 400 | 15.0% |
| Dipropylene glycol | 10.0% |
| Sodium lauroyl glutamate | 20.0% |
| POE(2) monostearic acid ester | 5.0% |
| Sodium palmoyl glutamate | 8.0% |
| Alkyl betaine | 2.0% |
| Disodium EDTA | 0.02% |
| Propylparaben | 0.1% |
| Methylparaben | 0.15% |
| Perfume | q.s. |
| Purified water | balance |

Formulation Example 7: Sunscreen

In this formulation example, a sunscreen (milky lotion) containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.2% |
| 1,3-Butylene glycol | 3.0% |
| Dipropylene glycol | 3.0% |
| Cyclomethicone | 5.0% |
| Dimethicone | 5.0% |
| Cetanol | 1.0% |
| Vaseline | 1.0% |
| Octyl methoxycinnamate | 5.0% |
| Titanium oxide | 2.0% |
| Zinc oxide | 2.0% |
| Sorbitan stearate | 1.0% |
| POE(20) sorbitan monostearic acid ester | 1.0% |
| Phenoxyethanol | 0.8% |
| Methylparaben | 0.1% |
| Perfume | q.s. |
| Purified water | balance |

Formulation Example 8: Lip Cream

In this formulation example, a lip cream containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.1% |
| Microcrystalline wax | 1.5% |
| Ceresin | 12.0% |
| Squalane | 10.0% |
| Decamethyltetrasiloxane | 10.0% |
| Diisostearyl malate | 5.0% |
| Candelilla wax | 2.0% |
| Vaseline | 8.0% |
| Glyceryl hydroxystearate | 2.0% |
| Menthol | 0.05% |
| Liquid paraffin | 1.0% |
| Tocopherol acetate | 0.1% |
| Tocopherol | 0.05% |
| Propylparaben | 0.1% |
| Perfume | q.s. |
| Purified water | balance |

Formulation Example 9: Shampoo

In this formulation example, a shampoo containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.2% |
| Cationized hyaluronic acid (Hyaloveil, manufactured by Kewpie Corporation) | 0.1% |
| Sodium POE(20) lauryl ether sulfate | 11.0% |
| Sodium lauroyl aspartate | 10.0% |
| Cocamidopropyl betaine | 4.0% |
| Cocamid monoethanolamine | 2.0% |
| Disodium EDTA | 0.1% |
| Sodium benzoate | 0.2% |
| Phenoxyethanol | 0.8% |
| Methylparaben | 0.1% |
| Perfume | q.s. |
| Purified water | balance |

Formulation Example 10: Hair Conditioner

In this formulation example, a hair conditioner containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.3% |
| Cationized hyaluronic acid (Hyaloveil, manufactured by Kewpie Corporation) | 0.2% |
| Stearyl alcohol | 4.0% |
| Cetanol | 1.5% |
| Hydroxyethylurea | 1.0% |
| Aminopropyldimethicone | 1.5% |
| Dimethicone | 0.5% |
| Hydrolyzed silk | 1.0% |
| 1,3-Butylene glycol | 1.0% |
| Glycerin | 3.0% |
| Cetyl 2-ethylhexanoate | 2.0% |
| Isocetyl myristate | 0.4% |
| L-Arginine | 0.1% |
| Trehalose | 0.1% |
| Sorbitol | 0.1% |
| Keratin peptide | 0.1% |
| POE(4) stearyl ether | 1.0% |
| Dimethylaminopropylamide stearate | 3.0% |
| Distearyldimethylammonium chloride | 0.2% |
| Sodium benzoate | 0.3% |
| Phenoxyethanol | 0.8% |
| Methylparaben | 0.1% |
| Perfume | q.s. |
| Purified water | balance |

Formulation Example 11: Soft Capsule

In this formulation example, a soft capsule containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 20% |
| Olive oil | 35% |
| Beeswax | 5% |
| Medium-chain fatty acid triglyceride | 5% |
| Gelatin | 25% |
| Glycerin | 10% |

Formulation Example 12: Powdered Medicine

In this formulation example, a powder medicine (granule) containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 10% |
| Lactose | 60% |
| Corn starch | 25% |
| Hypromellose | 5% |

Formulation Example 13: Soft Capsule

In this formulation example, a tablet containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 25% |
| Lactose | 24% |
| Crystalline cellulose | 20% |
| Corn starch | 15% |
| Dextrin | 15% |
| Silicon dioxide | 1% |

Formulation Example 14: Jelly Beverage

In this formulation example, a white peach jelly beverage in a spout pouch containing the carboxymethyl-group-containing modified hyaluronic acid obtained in Experimental Example 1 was prepared according to the following formulation.

| | |
|---|---|
| Carboxymethyl-group-containing modified hyaluronic acid (Experimental Example 1) | 0.20% |
| Xanthan gum | 1.00% |
| Carrageenan | 0.5% |
| Dextrin alcohol | 3.0% |
| Sucralose | 1% |
| Four-fold concentrated white peach juice | 5.00% |
| Citric acid | 0.60% |
| Sodium citrate | 0.20% |
| L-Ascorbic acid | 0.10% |
| Peach flavor | 0.20% |
| Purified water | balance |

The invention claimed is:

1. A method of producing a carboxymethyl-group-containing modified hyaluronic acid and/or a salt thereof, the method comprising a step of subjecting, in a water-containing solvent having a temperature of 30° C. or less, a dissolved raw material hyaluronic acid and/or a salt thereof to a reaction with a haloacetic acid and/or a salt thereof, the water-containing solvent comprising water, wherein the water-containing solvent does not comprise a water-soluble organic solvent.

2. The method of producing a carboxymethyl-group-containing modified hyaluronic acid and/or a salt thereof according to claim 1, wherein the haloacetic acid is chloroacetic acid and/or bromoacetic acid.

3. The method of producing a carboxymethyl-group-containing modified hyaluronic acid and/or a salt thereof according to claim 1, wherein a concentration of the hyaluronic acid in the water-containing solvent is 0.05 g/mL or more and 0.5 g/mL or less.

4. The method of producing a carboxymethyl-group-containing modified hyaluronic acid and/or a salt thereof according to claim 1, wherein the dissolved raw material hyaluronic acid and/or the salt thereof has a molecular weight of 4,000 or more and 4,000,000 or less.

5. The method of producing a carboxymethyl-group-containing modified hyaluronic acid and/or a salt thereof according to claim 1, wherein the obtained carboxymethyl-group-containing modified hyaluronic acid and/or salt thereof has a b value indicating a hue of a color of 5 or less.

6. The method of producing a carboxymethyl-group-containing modified hyaluronic acid and/or a salt thereof according to claim 1, wherein the reaction step provides a carboxymethyl-group-containing modified hyaluronic acid having a molecular weight of 800,000 or more.

7. The method of producing a carboxymethyl-group-containing modified hyaluronic acid and/or a salt thereof according to claim 6, wherein the reaction step provides a carboxymethyl-group-containing modified hyaluronic acid having a carboxymethylation ratio to disaccharide units constituting the hyaluronic acid of 5% or more and 200% or less.

8. The method of producing a carboxymethyl-group-containing modified hyaluronic acid and/or a salt thereof according to claim 1, wherein the reaction step provides a carboxymethyl-group-containing modified hyaluronic acid having a molecular weight of 4,000 or more and less than 800,000.

9. The method of producing a carboxymethyl-group-containing modified hyaluronic acid and/or a salt thereof according to claim 8, wherein the reaction step provides a carboxymethyl-group-containing modified hyaluronic acid having a carboxymethylation ratio to disaccharide units constituting the hyaluronic acid of 60% or more and 200% or less.

10. The method of producing a carboxymethyl-group-containing modified hyaluronic acid and/or a salt thereof according to claim 1, wherein a reaction time is 2 hours or more.

11. The method of producing a carboxymethyl-group-containing modified hyaluronic acid and/or a salt thereof according to claim 1, wherein the reaction step provides a carboxymethyl-group-containing modified hyaluronic acid having a molecular weight of 800,000 or more and a carboxymethylation ratio to disaccharide units constituting the hyaluronic acid of 40% or more and 200% or less.

12. The method of producing a carboxymethyl-group-containing modified hyaluronic acid and/or a salt thereof according to claim 1, wherein the reaction step provides a carboxymethyl-group-containing modified hyaluronic acid having a molecular weight of 4,000 or more and less than 800,000 and a carboxymethylation ratio to disaccharide units constituting the hyaluronic acid of 60% or more and 200% or less.

* * * * *